United States Patent [19]

Kawase et al.

[11] Patent Number: 5,324,635
[45] Date of Patent: Jun. 28, 1994

[54] METHOD AND APPARATUS FOR AUTOMATIC MEASUREMENT OF FLUORESCENCE

[75] Inventors: Masumi Kawase, Yono; Kyoko Imai, Katsuta; Hiroshi Hashimoto, Ibaraki, all of Japan

[73] Assignee: Hitcahi, Ltd., Tokyo, Japan

[21] Appl. No.: 397,853

[22] Filed: Aug. 24, 1989

[30] Foreign Application Priority Data

Aug. 26, 1988 [JP] Japan ................................ 63-210741

[51] Int. Cl.⁵ .......................................... G01N 33/535
[52] U.S. Cl. ........................................ 435/7.94; 435/3;
435/289; 435/968; 436/518; 436/8; 436/50;
436/172; 436/800; 436/805; 422/82.08;
250/459.1
[58] Field of Search ................... 422/63, 64, 82.08;
435/3, 7.9, 289, 968, 7.94; 436/800, 805, 829,
172, 8, 10, 50, 518; 250/458.1, 459.1, 461.1,
461.2; 356/306, 317, 318

[56] References Cited

U.S. PATENT DOCUMENTS

| | | | |
|---|---|---|---|
| 3,973,129 | 8/1976 | Blumberg et al. | 250/461.2 |
| 4,043,756 | 8/1977 | Sommervold . | |
| 4,271,123 | 6/1981 | Curry et al. | 436/805 X |
| 4,372,745 | 2/1983 | Mandle et al. | 436/805 X |
| 4,536,655 | 8/1985 | Barnes | 250/461.1 |
| 4,886,761 | 12/1989 | Gustafson et al. | 436/810 X |

FOREIGN PATENT DOCUMENTS 1588298 4/1970 France .
62-50662 3/1987 Japan .

OTHER PUBLICATIONS

Kelly et al., "Fluorometer for Flow Injection Analysis with Application to Oxidase Enzyme Dependent Reactions", *Anal. Chem.*, vol. 53, pp. 2110–2114, (1981).

Tiffany, Thomas O. "Fluorometry, Nephelometry, and Turbitity,", in Textbook of Clinical Chemistry, Norbert W. Tietz, Ed., W. B. Saunders Company, Philadelphia, (1986), pp. 88–89.

*Primary Examiner*—Esther L. Kepplinger
*Assistant Examiner*—Susan Wolski
*Attorney, Agent, or Firm*—Fay, Sharpe, Beall, Fagan, Minnich & McKee

[57] ABSTRACT

An analyzer has a reaction disk for holding a plurality of reaction containers and a fluorophotometer for measuring fluorescence stemming from solutions in the containers. Most of the containers contain solid phases attached with antibodies but at least one container does not contain any solid phase. In normal operation of the analyzer, a test sample containing antigens and a latently fluorescent reagent such as an antibody labeled by an enzyme are added to a container containing a solid phase. In this container, a fluorescent substance is created through an enzyme reaction. Light is irradiated on the container and the fluorescence emitted from the fluorescent substance is measured. While measuring test samples, fluorescence stemming from a reference sample, such as quinine sulfate, is measured to produce values for the reference sample by which measured values for the test samples are corrected. Prior to measuring general test samples by the analyzer, fluorescence stemming from a reference sample in a container removed of any solid phase is measured and compared with a setting value. If the results of the comparison indicate that the normal operation will be difficult to continue, then the sampling operation by the pipetter is discontinued.

3 Claims, 6 Drawing Sheets

METHOD AND APPARATUS FOR AUTOMATIC MEASUREMENT OF FLUORESCENCE

BACKGROUND OF THE INVENTION

This invention relates to a method and apparatus for automatic measurement of fluorescence and more particularly to an analytical method and apparatus applicable to measurement of a fluorescent substance created by adding a latently fluorescent reagent to a sample to be tested.

In the past, a radio-immunoassay method using radioisotopes has been employed widely in order to measure, with immunologic methods, a small amount of substances in a biological sample, but recently a measurement method using an enzyme or a liposome has been predominant.

An enzyme immunoassay method is disclosed in, for example, JP-A-62-50662. In this example, a complex of an antigen, an antibody and an enzyme is created on the surface of a bead and the intensity of fluorescence caused by an enzyme reaction, which develops when a substrate is brought into contact with the complex, is measured.

The above JP-A-62-50662 uses an ordinary fluorophotometer to measure reaction solutions and fails to refer to an apparatus using an automated reaction system and a fluorophotometer in combination.

On the other hand, in the field of automatic chemical analyzers, the analyzer itself changes (drifts) with time so that measured values are affected, by such a drift change, and therefore countermeasures against this problem have been contrived. For example, U.S. Pat. No. 4,043,756 discloses a method of photometry of light which is absorbed by reaction solutions of samples to be tested which are drawn into flow cells. Before carrying out measurements of the test samples, a reaction solution of a reference sample and a reagent blank are first measured with a view of correcting a standard curved, and a drift variation of the analyzer per se is corrected using a corrected standard curve.

When designing an immunoanalyzer by incorporating a fluorophotometer into an automatic analyzer, it is of significance to ensure high stability of the detection system and high reliability of results of measurement in the immunoanalyzer. In the measurement, quantitative measurement of a small amount of antigens or antibodies in a biological sample is needed and abnormality in performance of the optical system for fluorophotometry leads to impairment of analysis of small amounts. Further, degradation of the reagent is a factor in increasing measurement error in the analysis of small amounts.

The aforementioned U.S. Pat. No. 4,043,756 describes drift variations of the analyzer but does not consider the performance degradation of the optical system and the reagent degradation. A reference sample used in this literature is a reaction solution prepared by reacting the same element as a target element in a test sample in the same way. In immunoanalysis, however, it is difficult to obtain a chemically stable solution of a substance which may be used as a reference sample in reactions.

SUMMARY OF THE INVENTION

An object of this invention is to provide a method and apparatus which can decide automatically whether an analyzer capable of measuring fluorescence is maintaining proper performance.

Another object of this invention is to provide a method and apparatus which can produce highly accurate results of fluorophotometry of a target element in a sample to be tested.

Still another object of this invention is to provide a method and apparatus which can improve stability of measurement when quantitative measurement of concentration of antigens or antibodies in a test sample is effected indirectly by measuring fluorescence stemming from a fluorescent substance in a reaction solution which results from immunoreaction.

According to the invention, fluorescent substances are chosen corresponding to the number of target elements in a test sample container in a reaction container, and the intensity of fluorescence stemming from a reaction solution in the reaction container is measured by means of a fluorophotometer.

This can be done through the steps of measuring the intensity of fluorescence emitted by a reference sample, comparing a predetermined setting value with a measured value of the reference sample, and discontinuing the subsequent sampling operation by pipetting means when the results of comparison indicate that the measured value is smaller than the setting value.

When the results of comparison indicate that the measured value is larger than the setting value, the subsequent sampling operation by the pipetting means is allowed to continue and thereafter a reaction processing and a fluorophotometry processing for general test samples are carried out sequentially.

DESCRIPTION OF THE PREFERRED EMBODIMENTS

In an immunoanalysis apparatus to which the invention is applied, the lower limit of magnitude of measured signals necessary for the analysis of small amounts is first set through an input unit and stored in a memory unit. Used as a fluorescent reference sample is a solution of a chemically stable substance such as for example quinine sulfate. A sample to be tested (general test sample) and the fluorescent reference sample are pipetted into corresponding reaction containers in a movable train of reaction containers. While a latently fluorescent reagent is added to the reaction container containing the test sample, no latently fluorescent reagent is added to the reaction container containing the fluorescent reference sample so that fluorescence stemming from the solution itself may be measured. In this manner, the intensity of fluorescence which is substantially constant can be obtained reiteratively as long as the performance of the optical system remains constant.

Prior to fluorophotometry of reaction solutions based on general test samples, the intensity of fluorescence from the reference sample is measured and a measured value is compared with a setting value stored previously in a memory unit. When the intensity of fluorescence from the reference sample is below the setting value, indicating that the optical system is placed in a state which does not meet the condition for the analysis of small amounts, the subsequent pipetting of the test sample by means of a pipetter is discontinued to prevent invalid measurement. In such an event, the operator checks the light source and photoelectric detectors and replaces degraded components with new ones, as necessary, to enable the optical system to recover necessary function. After recovery of the function of the optical system, the pipetter is allowed to start sampling the general samples and a reaction disk is also allowed to start normal operation. Subsequently, test samples which have already been contained in several reaction containers on the reaction disk may be brought into the analysis processing under programmed control without being discarded.

When results of comparison between the measured value for the reference sample and the setting value indicate that the intensity of fluorescence stemming from the reference sample exceeds the setting value, indicating that the optical system is placed in a satisfactory state, the subsequent pipetting of test samples is allowed to continue.

In a preferred embodiment of the invention, the upper limit of values of fluorophotometry of a reagent blank is first set and stored. When the reagent blank value measured during the analysis of a plurality of test samples exceeds the upper limit, an alarm indicative of degradation of reagent is delivered, thus urging the operator to exchange the reagent with a new one.

Figure 2:
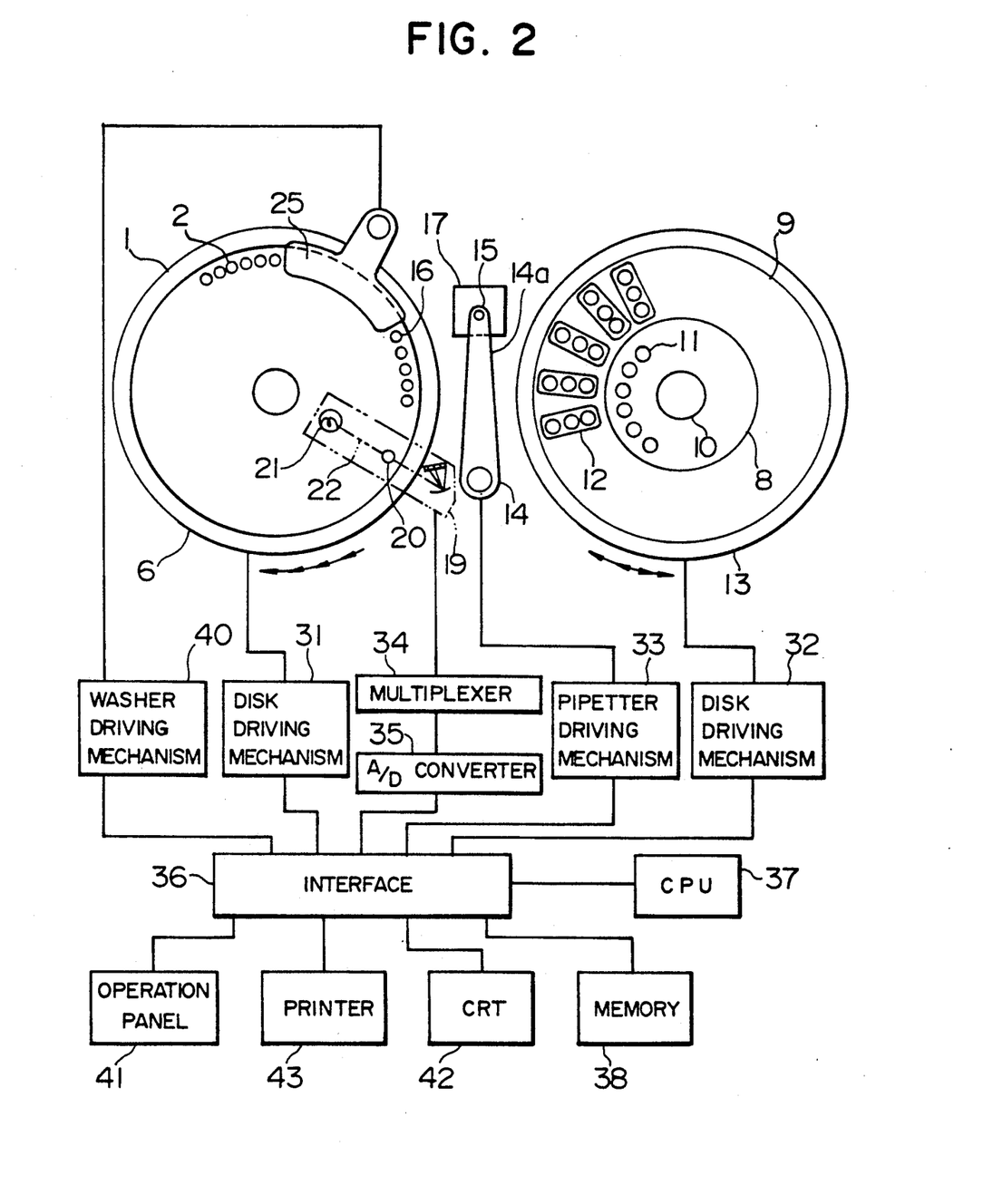
FIG. 2 is a schematic plan view illustrating an immunoanalysis apparatus for realizing the embodiment operable in accordance with the FIG. 1 flow chart.

An immunoanalysis apparatus to which the invention is applied may be constructed as shown in FIG. 2.

Referring to FIG. 2, a plurality of reaction containers 2 are arrayed on a rotary circular reaction disk 1 along its circumferential edge and the reaction disk 1 is rotated intermittently by means of a disk driving mechanism 31. The reaction container 2 suitable for fluorophotometry is made of a transparent material such as glass or acryl resin. A fluorophotometer 19 has a photometric position 20 which lies inside a reaction thermostatic tank 6.

The photometer 19 is of a multi-wavelength photometric type having a plurality of detectors and it faces the reaction container 2 so that when a reaction container 2 is at the photometric position 20 on the reaction disk 1, flux of light 22 emitted from light source lamp 21 transmits through that reaction container 2. Exciting, monochromatic light of a predetermined wavelength is irradiated on the solution in the reaction container from above or below the reaction container, and fluorescence emitted from the solution transmits through the side surface of the container and monochromatic light of a predetermined wavelength is selected and detected by a photomultiplier tube serving as the photoelectric detector.

A plurality of reagent cups 12 needed for a plurality of kinds of analysis items are held in array on a reagent disk 9 which is rotatable clockwise or counterclockwise. Each of the reagent cups 12 has a plurality of (for example, three) reagent solution storage chamber, and individual chambers store a first reagent, a second reagent and as necessary a third reagent which correspond to specified analysis items, respectively.

The reagent disk 9 and a sample disk 8 are rotated about a center shaft 10 by a number of pitches designated by a controller and this rotational operation is accomplished by a disk driving mechanism 32. With the above construction, a sample container 11 containing a target test sample and a required reagent cup 12 on the reagent disk 9 can be positioned and stopped at positions where the requisite test sample and reagent are drawn thereon. Sample cups 11 are maintained at a predetermined temperature inside an air thermoconstant tank. The reagent cups 12 are maintained at a low temperature of 10° C. or less by means of a cooling tank 13.

The reference sample or reference solution is formed of a liquid or solution containing a substance which is able to be excited to fluorescence by itself and for example, may be quinine sulfate, rhodamine B or water. In this embodiment, one of the reagent cups 12 contains a quinine sulfate solution at a predetermined concentration.

An arm 14a can be moved vertically (orthogonally to the sheet of drawing) and rotated about a shaft 14 by means of a pipetter driving mechanism 33. The arm 14a is mounted with a liquid charge/discharge nozzle or pipetting probe 15 which communicates with a cylinder in pipetter driving mechanism 33 through a liquid flow path. The probe 15 can be moved vertically at any one of the sample suction position on the sample disk 8, reagent suction position on the reagent disk 9, liquid discharge position 16 on the reaction disk 1 and probe washing position 17. During the first cycle of rotation of the reaction disk 1, the probe 15 may be operated to pipette a predetermined amount of sample form a sample cup 11 to a reaction container at a discharge position 16 and during the second cycle of rotation of the reaction disk 1, the probe 15 may be operated to pipette a predetermined amount of reagent from a reagent cup 12 to the reaction container at that discharge position 16.

Alternatively, the probe 15 may be operated to pipette a test sample and a first reagent during the first cycle of rotation of the reaction disk 1 and to pipette a second reagent and as necessary a third reagent during the second and ensuing cycle of rotation of the reaction disk.

When proceeding with an analysis operation of a general test sample such as a blood serum test sample, solid phases attached with antibodies (or antigens) corresponding to individual analysis items i.e., kinds of antigens or antibodies are first stored in reaction containers. For example, a bead can be used as a solid phase with, the surface of the bead coated in advance with, for example, specified antibodies.

When a reaction container 2 storing a solid phase attached with antibodies reaches a discharge position 16, a sample drawn into the probe 15 from a sample cup 11 is discharged into that reaction container. After discharging, the interior and exterior of the probe 15 are washed by means of a washing unit also designated by reference numeral 17. Subsequently, the probe 15 draws in a reagent solution for immunoreaction from a selected reagent cup 12 and adds the reagent to the same reaction container 2, while staying at that discharge position 16. The immunoreaction reagent solution contains antibodies labeled by an enzyme. Thereafter, the reaction disk 1 is advanced clockwise by one step. Similar sampling operations are sequentially undertaken by the probe 15, serving as a pipetting mechanism, for the following reaction containers.

In the reaction container containing the test sample added with the immunoreaction reagent (that is, a first reagent), an antigen used as a target element in the sample couples to an antibody attached to the bead and the antibody labeled by an enzyme couples to the coupled antigen. Thus, immunocomplexes are created on the bead through antigen/antibody reaction. When the reaction container containing the immunocomplex reaches a region of a washer 25 having a plurality of nozzles, a liquid containing part of the reagent which has not been reacted is discharged from the reaction container and accordingly the bead having the immunocomplex remains in the reaction container. In the next step, a cleansing solution is charged into the reaction container, and the cleansing solution is then discharged after cleansing, leaving the bead having the immunocomplex in the reaction container. The above bead washing operation is repeated a plurality of times. The washer 25 is operated for vertical movement and charging/discharging by means of a washer driving mechanism 40.

When the reaction disk 1 is further advanced and the reaction container 2 containing the washed bead reaches a discharge position 16, the probe 15 is operated to draw in a latently fluorescent reagent as a second reagent from a specified reagent cup 12 and adds the second reagent to the bead. As the latently fluorescent reagent, a solution may be used containing a substrate which is able to turn into a fluorescent substance. In the reaction container 2, the substrate reacts with the enzyme attached to the solid phase so as to turn into the fluorescent substance.

When the reaction disk 1 is further advanced stepwise and the reaction container 2 containing the fluorescent substance reaches the photometry position 20, the container is irradiated by means of the fluorophotometer 19 to measure the intensity of fluorescence stemming from the reaction solution in the container. Output signals produced from a plurality of photodetectors of the photometer 91 are applied to a multiplexer 34 at which only a signal based on a requisite monochromatic light is selected. The selected signal is converted by an analog/digital converter 35 into a digital signal which in turn is stored into a memory unit 38 such as a random access memory or a floppy disk through an interface 36 under the control of a central processing unit (CPU) 37.

Prior to carrying out a series of analysis operations described previously for a blood sample as the general test sample with the analyzer shown in FIG. 2, the lower limit for deciding the performance of the optical system and the upper limit for deciding degradation of the reagent are set in the analyzer. A setting value for deciding the performance of the optical system and an acceptable upper limit value for deciding the reagent degradation are inputted by the operator, who is manipulating the keyboard of an operation panel 41, and stored in the memory unit 38 under the control of the CPU 37.

Figure 3:
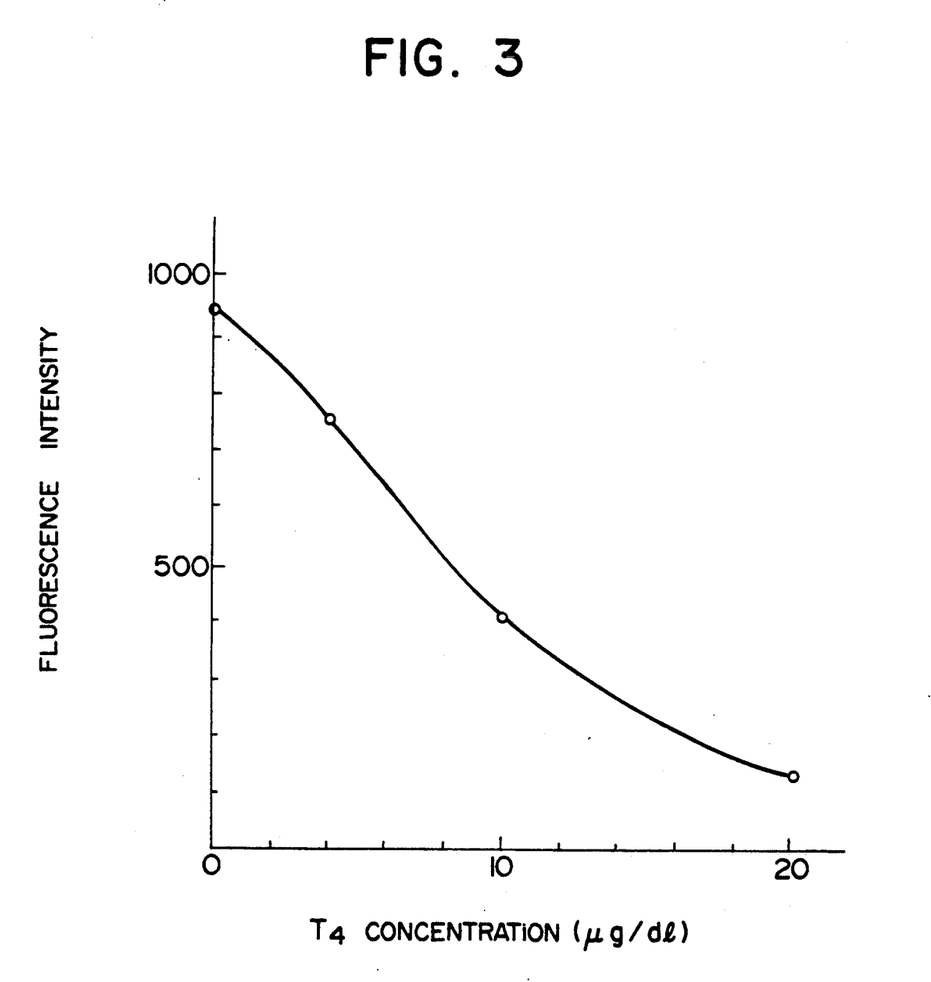
FIG. 3 is a graph showing an example of a standard curve for $T_4$ (thyroxine).
Figure 4:
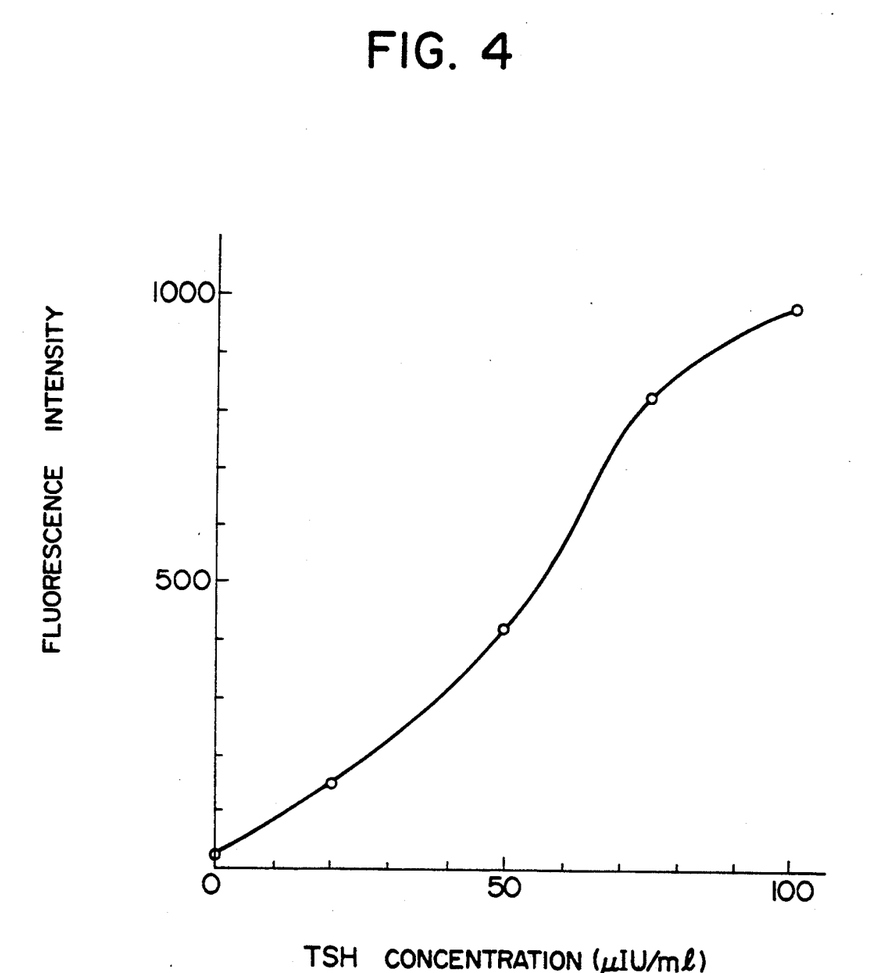
FIG. 4 is a graph showing an example of a standard curve for TSH (thyroid stimulating hormone).

For convenience of description, an example will now be described where $T_4$ (thyroxine) and TSH (thyroid stimulating hormone) in a blood serum are measured. These analysis items are displayed on the screen of a CRT 42 and selected. Reaction containers 2 storing beads coated with antibodies needed for respective analysis items are set on the reaction disk 1. For reference sample measurement and reagent blank, reaction containers devoid of bead are set. The correspondence between each of the reaction containers arrayed in sequence on the reaction disk and each of the analysis item, reference sample and reagent blank is set up and stored in the controller. Also, standard curves or working curves corresponding to respective analysis items are determined and stored in the controller prior to measurement. FIG. 3 shows an example of a standard curve for $T_4$ and FIG. 4 an example for TSH.

The operation of the analyzer shown in FIG. 2 will now be described with reference to FIG. 1.

In step 101, the operator pushes the start key on the operation panel 41 of the analyzer to start the analysis operation. In the analysis apparatus, the arm 14a of the pipetting mechanism is first operated to pipette a predetermined amount of quinine sulfate solution, standing for the fluorescent reference sample, from a reagent cup 12 containing the quinine sulfate into the first reaction container (step 102). Thereafter, an operation for pipetting a general test sample from a sample cup 11 corresponding to the following reaction container 2 is started (step 103).

The pipetting mechanism is controlled by the controller such that neither a latently fluorescent reagent containing a substrate nor an immunoreaction start reagent is added to the reaction container filled with the quinine sulfate. When this reaction container containing the reference sample reaches the photometry position 20, fluorescence stemming from the reference sample is measured by means of the fluorophotometer 19 (step 104). The photometry uses an exciting wavelength of 380 nm to measure a fluorescent wavelength of 460 nm. The same exciting wavelength as above is applied to any analysis items of a general test sample.

In step 105, the controller decides whether a measured value of the intensity of fluorescence stemming from the reference sample exceeds a predetermined setting value. If the results of comparison indicate that the measured value of the fluorescence emitted from the reference sample is less than the setting value, the procedure proceeds to step 106. At that time, the controller issues a command for stopping operation to individual mechanisms including the pipetting mechanism 33 and reaction disk 1, and as a result, the analysis operation of the analysis apparatus is discontinued (step 107) and at the same time an alarm indicated of unsuitability of the optical system for the analysis of small amounts is displayed on the screen of the CRT 42 (step 108). In this case, the operation of the analysis apparatus ends (step 109). Observing the alarm display, the operator checks the fluorophotometer 19 and exchanges the light source lamp or the photoelectric detectors, if degraded, with new ones to restore the performance of the analyzer.

If the results of comparison in step 105 indicate that the intensity of fluorescence stemming from the reference sample is greater than the setting value, the pipetting mechanism 33 continues pipetting general test sample s(step 110). No sample is pipetted in a reaction container for blank measurement but a latently fluorescent reagent is added to the blank measurement reaction container in the same amount as that added to the general test sample. A sample solution is pipetted, by in an amount of 50 μl, from a sample cup 11 to a reaction container for general test sample and thereafter an immunoreaction reagent is 200 μl pipetted in that reaction container (step 111). For example, as the immunoreaction reagent, a solution containing an antibody for each analysis item labeled by an enzyme is used.

In the reaction container 2 on the reaction disk 1, an antigen/antibody reaction proceeds under the condition of heat insulation at 37° C. to create antigen/antibody reaction complexes on a bead. The reaction container reaches the region of the washer 25 thirty minutes after the start of the reaction. At the region, part of the solution containing substances which have not been reacted is discharged from the reaction container, 500 ml a cleansing solution is charged into the reaction container and the used cleansing solution is finally discharged from the reaction container (step 112). The above bead washing operation using the cleansing solution is repeated three times.

On the other hand, the pipetting mechanism 14 operates to pipette the reference sample solution and the latently fluorescent reagent into corresponding reaction containers for reference sample and reagent blank which are disposed at predetermined intervals in the train of reaction containers (step 113).

The pipetting mechanism 14 then pipettes a latently fluorescent reagent into the reaction container for general test sample washed in the step 112. As the latently fluorescent reagent, a substrate and a buffer solution are added by 50 μl and 200 μl, respectively, (step 114) and an enzyme reaction proceeds for 30 minutes at 37° C. In this example, a solution of 4-methylumbelliferyl phosphate is used as the substrate and alkali phosphatase is used as the enzyme to proceed with the enzyme reaction. Through this reaction, 4-methylumbelliferone is created which is a fluorescent substance.

In step 115, it is decided whether the reaction container positioned at the photometry position 20 is for the reference sample, and similarly, it is decided in step 116 whether the reaction container reaching the photometry position is for the reagent blank. For the reaction solution of general test sample, the intensity of fluorescence stemming therefrom is measured 15 minutes after the step 114 (step 117). The amount of 4-methylumbelliferone created in the reaction solution depends on the amount of antigen/antibody reaction complexes on the bead.

When the reaction container for reference sample reaches the photometry position 20, the procedure branches from step 115 to step 122, at which the intensity of fluorescence stemming from the quinine sulfate solution is measured. A correction coefficient for a standard curve stored in advance is calculated on the basis of a measured value of the intensity of fluorescence stemming from the reference sample (step 123) and used for correcting the standard curve (step 124)

When the reaction container for reagent blank reaches the photometry position 20, the procedure branches from step 116 to step 118, at which the intensity of fluorescence stemming from the reagent blank that is unaffected by the antigen/antibody reaction complex is measured, and the fluorescence intensity is compared to an acceptable value stored in advance (step 119). If a value measured for the reagent blank exceeds the acceptable value, an alarm indicative of degradation of the latently fluorescent reagent is displayed on the screen of the CRT 42 (step 120). This alarm is printed out by a printer 43 upon delivery of the results of the analysis in step 126.

If the value measured for reagent blank is less than the acceptable value, the fluorophotometry of the reaction solution of general test sample follows and the measured value of the intensity of fluorescence stemming from the reaction solution is corrected on the basis of a reagent blank value (step 121) and then compared with the standard curve. Even if the reagent blank value is determined to be greater than the acceptable value, the analysis apparatus may be allowed not to be discontinued but to continue analyzing general test samples, provided that the operator fulfils exchange of the substrate solution in accordance with the alarm display.

In step 125, element concentrations corresponding to the measured values for the general test samples are calculated from the standard curve corrected on the basis of the measured value for the reference sample and the measured value for the reagent blank, and in step 126 analysis values of individual test samples are delivered. In this example, the ratio between a photometric value measured for the reference sample when preparing a standard curve and a photometric value measured for the reference sample immediately before conducting photometry of the test sample is used to correct the standard curve itself, but alternatively a value measured for the test sample may first be corrected by the correction coefficient and then applied to the initial standard curve for the purpose of calculating concentration of analysis elements. When the analysis operations for all test samples are completed, operation of individual mechanisms of the analysis apparatus ends (step 127).

EXPERIMENTAL EXAMPLE

Figure 1:
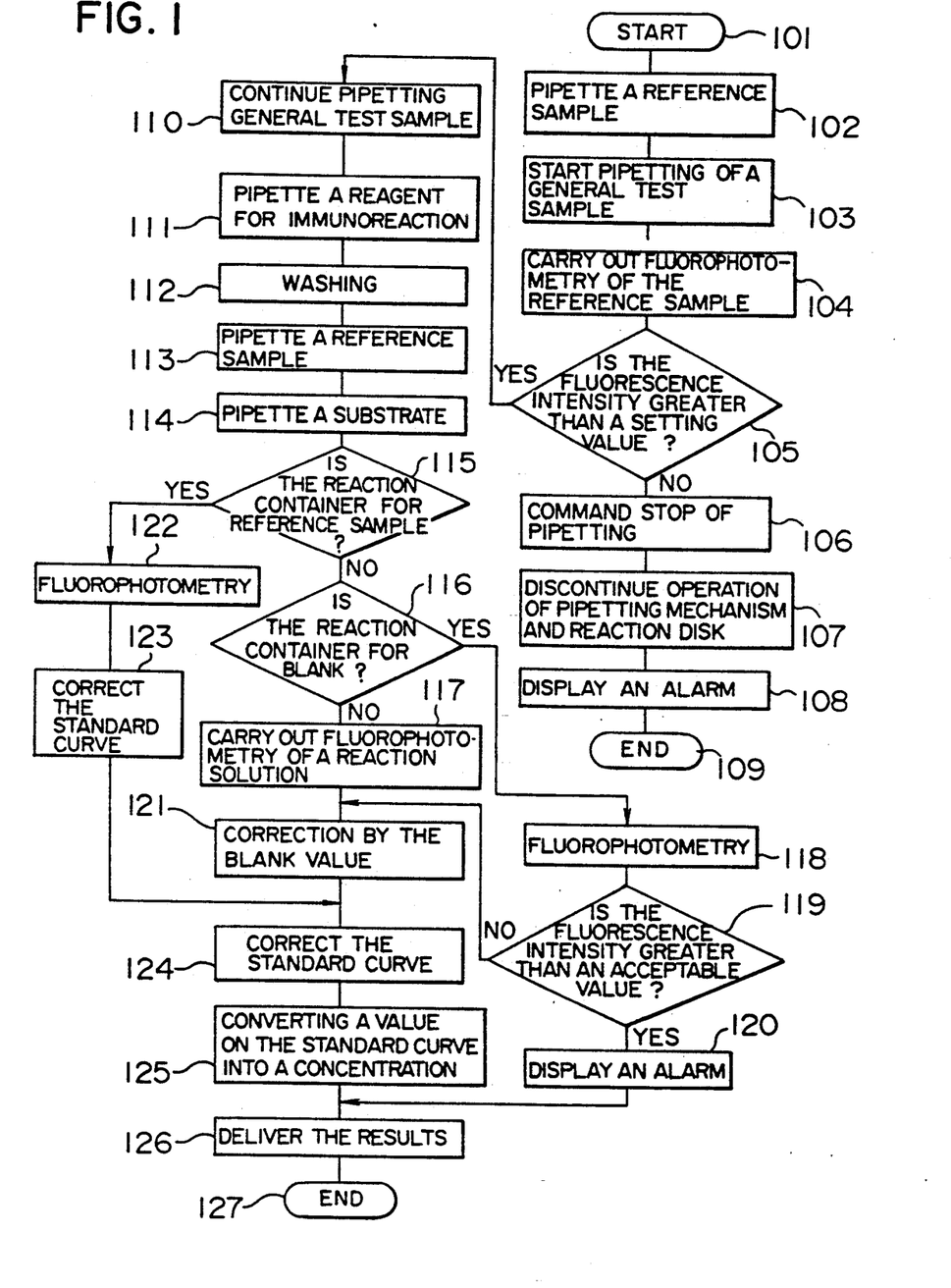
FIG. 1 is a flow chart for explaining the operation of an embodiment of the invention.

The same control blood serum was pipetted into 20 reaction containers and $T_4$ and TSH were measured in accordance with the flow shown in FIG. 1. Results of measurement are shown in Table 1. Net data, representative of measured values before correction, for individual test samples is suffixed with A and data after correction is suffixed with B. The reference sample was quinine sulfate solution, and a photometrical value measured for the quinine when experimentally obtaining data in Table 1 was 170.3 and a photometrical value measured for the quinine when preparing the standard curve was 165.4. Accordingly, the correction coefficient is 165.4/170.3.

TABLE 1

| Sample No. | $T_4$ (A) | $T_4$ (B) | TSH (A) | TSH (B) |
|---|---|---|---|---|
| 1 | 403.2 | 391.6 | 262.0 | 254.5 |
| 2 | 402.8 | 391.2 | 261.1 | 253.6 |
| 3 | 404.5 | 392.9 | 263.3 | 255.7 |
| 4 | 401.0 | 389.5 | 261.7 | 254.1 |
| 5 | 402.9 | 391.3 | 262.5 | 254.9 |
| 6 | 403.1 | 391.5 | 262.4 | 254.9 |
| 7 | 401.6 | 390.0 | 261.3 | 254.3 |
| 8 | 403.7 | 392.1 | 261.9 | 254.4 |
| 9 | 404.1 | 392.5 | 263.4 | 255.8 |
| 10 | 404.3 | 392.7 | 260.6 | 253.1 |
| 11 | 405.8 | 394.1 | 261.8 | 254.3 |
| 12 | 400.9 | 389.4 | 262.9 | 255.3 |
| 13 | 401.3 | 389.8 | 263.7 | 256.1 |
| 14 | 403.2 | 391.6 | 260.4 | 252.9 |
| 15 | 404.6 | 393.3 | 261.7 | 254.2 |
| 16 | 400.2 | 388.7 | 260.2 | 252.7 |
| 17 | 402.5 | 390.9 | 262.4 | 254.9 |
| 18 | 403.4 | 391.8 | 264.0 | 256.4 |
| 19 | 401.4 | 389.9 | 263.1 | 255.5 |
| 20 | 404.2 | 392.6 | 263.4 | 255.8 |

After data in Table 1 was measured, the same control blood serum was pipetted into 10 reaction containers and subjected to analysis measurement similarly to the precedence. Net data for individual test samples thus obtained is suffixed with A' and data after correction is suffixed with B'. In this measurement, a photometrical value for the reference sample was 175.6 and results of the measurement are shown in Table 2. Since the photometrical value measured for the quinine sulfate solution when preparing the standard curve is 165.4, the correction coefficient used for obtained data in Table 2 is 165.4/175.6.

TABLE 2

| Sample No. | $T_4$ (A') | $T_4$ (B') | TSH (A') | TSH (B') |
| --- | --- | --- | --- | --- |
| 1 | 423.5 | 398.9 | 268.8 | 253.2 |
| 2 | 415.4 | 391.3 | 269.7 | 254.0 |
| 3 | 416.7 | 392.5 | 269.2 | 253.6 |
| 4 | 415.7 | 391.6 | 269.9 | 254.2 |
| 5 | 418.8 | 394.5 | 271.7 | 255.9 |
| 6 | 414.9 | 390.8 | 269.5 | 253.8 |
| 7 | 416.8 | 392.6 | 270.4 | 254.7 |
| 8 | 415.4 | 391.3 | 271.3 | 255.5 |
| 9 | 416.3 | 392.1 | 268.7 | 253.1 |
| 10 | 416.2 | 392.0 | 270.2 | 254.5 |

For $T_4$, an average value $\bar{B}$ of the corrected values in Table 1 is 391.4 and an average value $\bar{B}'$ of the corrected values in Table 2 is 391.9, demonstrating that even when the measurement is not carried out on the same line, the influence of drift of the analysis apparatus can be removed to ensure highly reproducible measurement.

A second embodiment of the invention will now be described. In this embodiment, the immunoanalysis apparatus shown in FIG. 2 is also used. As the reference sample, a rhodamine B solution is used and a cup containing the reference sample is disposed on the reagent disk 9. The analyzer is operated in accordance with a flow similar to that shown in FIG. 1 to measure $T_4$ and TSH. No latently fluorescent reagent is added to the rhodamine B solution and the intensity of fluorescence stemming from the rhodamine B itself is measured. In this embodiment, the wavelength of exciting light for the reference sample is 550 nm and the wavelength of fluorescence excited from the reference sample is 590 nm.

In connection with the second embodiment, reproducibility of measurement was examined similarly to the previous embodiment. Ten samples of the same control blood serum were measured twice at different times. The value of fluorescence intensity measured for the reference sample of rhodamine B when preparing the standard curve was 451.7, the value measured for the reference sample when conducting the first measurement of the control blood serum was 438.2; and the value measured for the reference sample when conducting the second measurement of the control blood serum was 420.8. When measured values for test samples are corrected using the measured value for the reference sample and the measured value for the reagent blank, an average value of measured values in the first measurement was 382.1 and an average value of measured values in the second measurement was 382.7. Thus, even with rhodamine B used as the reference sample, the influence of drift can be removed and the difference between batches can be excluded.

A third embodiment of the invention will now be described. In this embodiment, the immunoanalysis apparatus shown in FIG. 2 is also used. As the reference sample, water is employed in this embodiment. The analysis apparatus is operated in accordance with a flow similar to that shown in FIG. 1 to measure $T_4$ and TSH. In this embodiment, addition of any latently fluorescent reagent is not effected, either, and the intensity of fluorescence stemming from water itself is measured. The wavelength of exciting light for the water serving as the reference sample is 380 nm and the wavelength of fluorescence excited from the reference sample is 470 nm.

In connection with the third embodiment, reproducibility of measurement was also examined. Ten samples of the same control blood serum were measured twice at different times. The value of fluorescence intensity measured for the reference sample of water when preparing the standard curve was 95.56, the value measured for the reference sample when conducting the first measurement of the control blood serum was 93.24, and the value measured for the reference sample when conducting the second measurement was 91.73. When measured values for test samples are corrected using the measured values for reference sample, an average value for $T_4$ was 393.0 in the first measurement and 391.0 in the second measurement and an average value for TSH was 289.7 in the first measurement and 289.6 in the second measurement.

Figure 5:
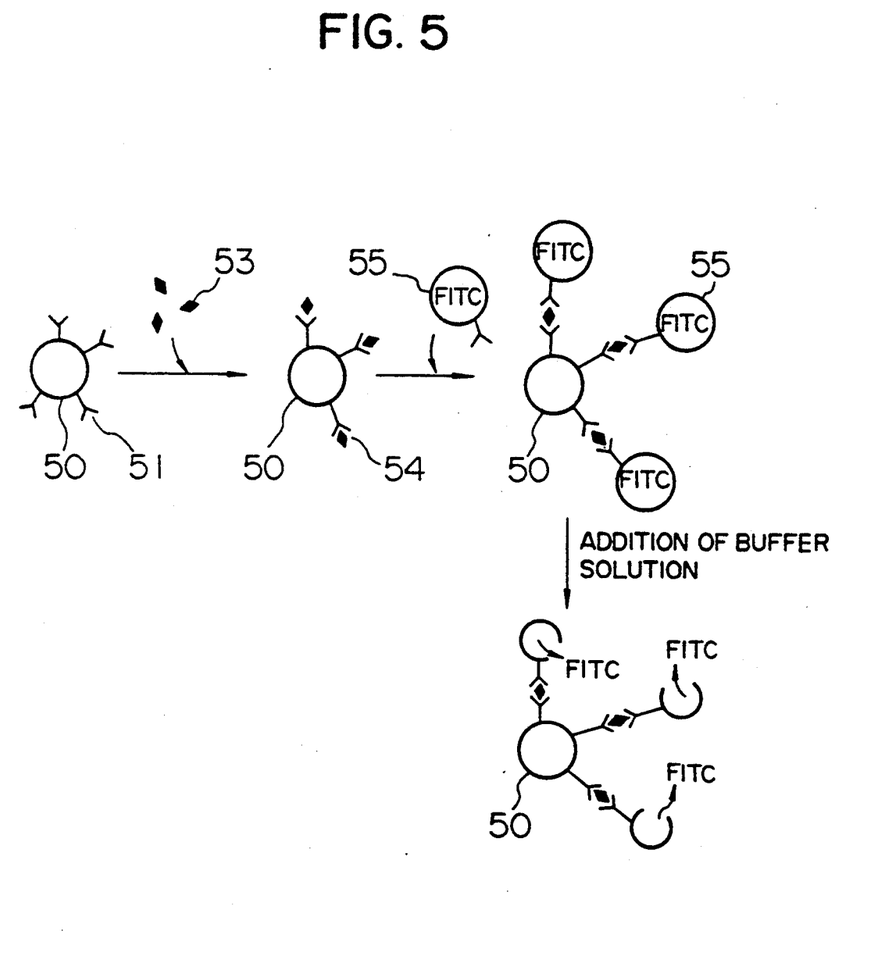
FIG. 5 is a schematic representation useful for explaining the reaction in a fourth embodiment of the invention.
Figure 6:
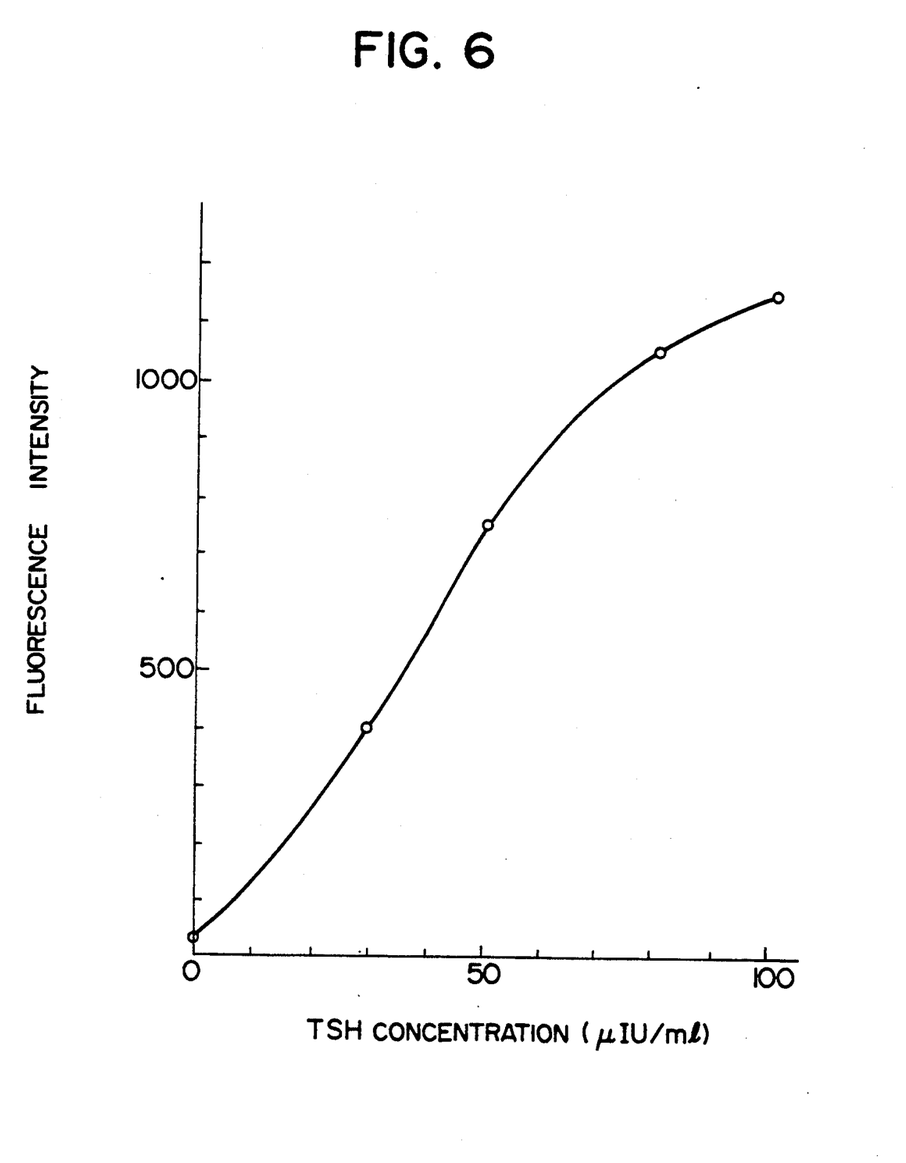
FIG. 6 is a graph showing an example of a standard curve for TSH used in the fourth embodiment.

A fourth embodiment of the invention will now be described. In this embodiment, not the substrate but liposomes sensitized by antibodies are used as the latently fluorescent reagent. This embodiment will be explained by referring to, for example, TSH as a measurement item. The analysis apparatus shown in FIG. 2 is also used and a reference sample of quinine sulfate and a solution of dispersed liposomes each having sealed-in FITC serving as a fluorescent marker are set on the reagent disk 9. Anti-TSH antibodies are attached to the surface of the liposome. As shown in FIG. 5, the same anti-TSH antibodies 51 as above are attached to the surface of a bead contained in a reaction container 2. Ten samples of control blood serum are set on the sample disk 8. An example of a standard curve prepared in advance is shown in FIG. 6.

In this embodiment, the operation of the analysis apparatus also follows the steps 101 to 113 in FIG. 1. In step 105, the value measured for the reference sample of quinine sulfate is determined to be greater than the setting value. When the control blood serum is added in the reaction container 2, antigens 53 (TSH) in the blood serum sample couple to the antibodies 51 on the bead 50 to create antigen/antibody reaction complexes 54. Thereafter, a reagent containing liposomes 55 sensitized by antibodies is added.

Thirty minutes after the start of an immunoreaction, the washer 25 operates to remove part of the reagent and part of the sample which have not been reacted in the reaction container, and after washing, 500 μl a buffer solution containing a surfactant is added in the reaction container. This ruptures the enclosure of the lipsome 55 and the sealed-in FITC flows out. The reaction container containing this reaction solution is positioned at the photometry position 20 and fluorophotometry is then carried out.

The value measured for the test samples is corrected using the measured values for the reference sample and the reagent blank in a way shown in the flow chart of FIG. 1. The correction coefficient for a standard curve based on the fluorophotometry of the reference sample was 165.4/175.4. The average value of fluorescence intensity of measured values for 10 analyzed TSH samples was 270.2 and the corrected average value was 254.8.

We claim:

1. An analysis method of an antigen or antibody analyte in a test sample, comprising the steps of:
    preparing a reference solution comprising a chemically stable fluorescent substance selected from the group consisting of quinine sulfate, rhodamine B and water to be used for checking an optical system having a fluorophotometer;
    supplying said reference solution to a reference container and positioning said reference container in an excitation light of the fluorophotometer;
    comparing a value of intensity of fluorescence of the reference solution measured by said fluorophotometer with a predetermined set value of intensity of fluorescence, said predetermined set value being a substantially minimum value in a range in which the optical system effectively functions for fluorescence measurement;
    indicating that the optical system is in an improper condition when the measured value for the reference solution is not greater than the predetermined set value;
    using said fluorophotometer only when the measured value is greater than the predetermined set value;
    reacting a solid phase on which is immobilized an antibody or an antigen which specifically binds to said analyte with said analyte contained in said test sample to form an immunocomplex in a reaction container,
    reacting and labeling said immunocomplex with an enzyme-labeled antibody that specifically binds to said analyte;
    adding a fluorogenic substrate specific for said enzyme into said reaction container to form a reaction solution;
    measuring and outputting a signal indicating the intensity of fluorescence of said reaction solution with said fluorophotometer; and
    receiving and processing the output signal to provide a quantitative measurement of concentration of said analyte.

2. A method according to claim 1, further comprising the steps of:
    preparing a reagent blank by adding an aliquot of only said fluorogenic substrate into a predetermined container and positioning the predetermined container in the excitation light of the fluorophotometer;
    obtaining a measured value of intensity of fluorescence of the reagent blank from the fluorophotometer for the predetermined container;
    comparing the measured value of the reagent blank measured by the fluorophotometer with a predetermined upper limit of intensity of fluorescence; and
    indicating that the reagent blank is degraded when the measured value is greater than the predetermined upper limit.

3. A method according to claim 1, further comprising the steps of:
    determining a first measured value of fluorescence emitted from the reaction solution;
    determining a second measured value of fluorescence emitted from said reference solution by measuring the intensity of fluorescence of said reference solution in mid course of measurement of a plurality of the reaction solutions; and
    correcting said first fluorescence measured value on the basis of said second fluorescence measured value.

* * * * *